United States Patent [19]

Ichikawa et al.

[11] 4,096,186
[45] Jun. 20, 1978

[54] PROCESS FOR RACEMIZING OPTICALLY ACTIVE AMINO COMPOUNDS

[75] Inventors: Yataro Ichikawa; Koji Nakagawa; Eishin Yoshisato, all of Iwakuni, Japan

[73] Assignee: Teijin Limited, Japan

[21] Appl. No.: 590,944

[22] Filed: Jun. 27, 1975

[30] Foreign Application Priority Data

Jun. 29, 1974 Japan ................................. 49-73843

[51] Int. Cl.$^2$ ...................... C07C 91/04; C07C 91/14; C07C 91/16
[52] U.S. Cl. ............................ 260/584 R; 260/563 R; 260/563 C; 260/570.6; 260/570.5 CA
[58] Field of Search ............ 260/584 R, 585 B, 583 R

[56] References Cited

U.S. PATENT DOCUMENTS

| 2,608,583 | 8/1952 | Aschner | 260/570.8 |
| 2,797,243 | 6/1957 | Hartgerink | 260/570.8 |
| 3,390,184 | 6/1968 | Moss et al. | 260/585 B |
| 3,766,184 | 10/1973 | Johansson et al. | 260/585 B X |

OTHER PUBLICATIONS

Bauer et al., "Chem. Abstracts", vol. 52, Ab. No. 9014h.

Primary Examiner—Daniel E. Wyman
Assistant Examiner—John J. Doll
Attorney, Agent, or Firm—Wenderoth, Lind & Ponack

[57] ABSTRACT

A process for racemizing optically active amino compounds, which comprises contacting an optically active compound of the general formula

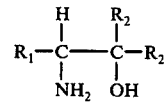

wherein $R_1$ is an alkyl, cycloalkyl, substituted or unsubstituted phenyl, or non-aromatic heterocyclic group, and $R_2$ is a hydrogen atom or an alkyl or substituted or unsubstituted phenyl group, with ammonia and hydrogen in the presence of a hydrogenation catalyst.

8 Claims, No Drawings

PROCESS FOR RACEMIZING OPTICALLY ACTIVE AMINO COMPOUNDS

This invention relates to a process for recemizing optically active amino compounds of the following general formula

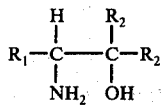

wherein $R_1$ is an alkyl group, cycloalkyl group, substituted or unsubstituted phenyl group or non-aromatic heterocyclic group, and $R_2$ is a hydrogen atom, alkyl group or substituted or unsubstituted phenyl group.

A compound of formula [I] in which $R_1$ is an ethyl group and $R_2$ is a hydrogen atom is 2-amino-1-butanol. Dextrorotary d-2-amino-1-butanol is a raw material for Ethmbutol which is useful as an antituberculous agent, whereas levorotary l-2-amino-1-butanol has no utilitarian value.

No industrial process has ever been proposed for racemizing optically active 2-amino-1-butanol, and the l-2-amino-1-butanol has been discarded as useless. This is partly responsible for the high cost of Ethambutol. Furthermore, no method has generally been known for racemizing compounds of formula [I] above.

It is an object of this invention therefore to provide a process for racemizing one of optical antipodes of an amino compound which has low utilitarian value thereby to give the other optical antipode having high utilitarian value.

Another object of this invention is to provide a process for racemizing optically active amino compounds of formula [I], especially racemizing levorotary amino compounds of formula [I], to convert them to dectrorotary amino compounds.

The above objects can be achieved in accordance with this invention by a process for racemizing optically active amino compounds which comprises contacting an optically active amino compound of the following formula

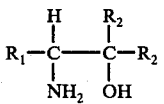

wherein $R_1$ is an alkyl, cycloalkyl, substituted or unsubstituted phenyl group, or non-aromatic heterocyclic group, and $R_2$ is a hydrogen atom, alkyl group or substituted or unsubstituted phenyl group, with ammonia and hydrogen in the presence of a hydrogenation catalyst.

According to the process of this invention, optically active amino compounds of formula [I] can be racemized within short periods of time to obtain industrially useful optical antipodes of amino compounds.

The catalyst used in the process of this invention is any catalyst having activity in hydrogenation. Preferred catalysts have the ability to induce hydrogenation and dehydrogenation. Examples of such catalysts are reducible metals such as nickel, cobalt or copper, and noble metals such as platinum, palladium, ruthenium or rhenium. Of these, cobalt-type hydrogenation catalysts are especially effective. Examples are reduced cobalt, and Urushibara cobalt. The reduced cobalt catalyst is particularly superior.

We have found that by adding a small amount of at least one other metal or metal oxide to the above cobalt-type hydrogenation catalyst, the degree of racemization can be increased, and the recovery ratio of the desired amino compound can be further increased.

Examples of the other metal or metal oxide suitable for use in this invention are iron, manganese, magnedium, aluminum, zinc, barium, cesium, thorium, cerium, zirconium, lanthanide and uranium, and oxides of these metals. Of these, iron and iron oxide are especially preferred.

The amount of the other metal or metal oxide to be added varies according to the type of the metal, the form of the catalyst, or the method for preparation of the catalyst (for example, the catalyst calcining temperature), etc. In the case of iron, the atomic ratio of iron to cobalt is 0.01-0.5, preferably 0.01-0.3, to 1. If the amount is less than this range, the effect of adding the other metal or metal oxide is small, and if it exceeds this range, side-reactions such as a decomposition reaction occur in increasing proportions, and the rate of racemization decreases.

The reduced cobalt catalyst containing the above additive can be prepared by various catalyst preparation methods. For example, a precipitating method and a calcining method are preferred.

The precipitating method, for example, comprises neutralizing a mixed solution of a cobalt salt and a salt of the additive metal exemplified above, with an aqueous solution of an alkali such as sodium hydroxide, sodium carbonate or ammonium carbonate to form a precipitate, washing the precipitate with water, drying or calcining it, and then reducing it in a stream of hydrogen gas at a temperature of 250° to 450° C.

The calcining method, on the other hand, involves pyrolyzing the above salt mixture to convert it to its oxide, and reducing the oxide in a stream of hydrogen gas at a temperature of 250° to 450° C.

The catalyst used in this invention may be supported on a known carrier such as silica, alumina, diatomaceous earth, kaolin, carborundum or silicon carbide.

The reaction temperature used in the process of this invention is affected by the type of the catalyst used, etc. Usually, it is 100° to 300° C., preferably 120° to 250° C.

The suitable amount of ammonia used in the process of this invention is usually at least 3 moles, preferably at least 5 moles, per mole of the optically active amino compound.

The reaction in accordance with this invention can be performed either in the vapor phase or in the liquid phase. Preferably, it is carried out in the liquid phase.

The reaction can be carried out in the presence of a solvent. Examples of usable solvents are hydrocarbons such as n-pentane, n-hexane or n-heptane, ethers such as diethyl ether, diisopropyl ether, dioxane or tetrahydrofuran, and alcohols such as methanol, ethanol, isopropyl alcohol or n-propyl alcohol, all of which are inert to the reaction. The amount of the solvent is not particularly restricted.

When the reaction is carried out in the liquid phase, the process using a pressure reactor can be performed either continuously or batchwise. The reaction pressure is desirably 100 to 600 atmospheres, although differing according to such factors as the reaction temperature, the type of the starting materials, the proportions of the starting materials, or the presence or absence of a solvent.

In the reaction of this invention, the partial pressure of hydrogen is preferably 10 to 150 atmospheres, especially preferably 30 to 100 atmospheres.

On the other hand, when the reaction is carried out in the vapor phase, the pressure may either be a reduced, atmospheric, or elevated pressure. Generally, it is desirable that the reaction is carried out at atmospheric pressure or at a pressure near it. The reaction in the vapor phase can be performed by vaporizing the starting optically active amino compound, mixing it with ammonia gas and then with hydrogen gas, heating the resulting gaseous mixture to a temperature in the above-specified range, and contacting it with the above catalyst.

The racemization of the amino compound of formula [I] in accordance with the process of this invention, according to the presumption of the inventors of the present application, goes through an intermediate of the following formula

wherein $R_1$ and $R_2$ are the same as defined hereinabove. It is presumed that the carbon atom to which the nitrogen atom is attached in the intermediate of formula [II] is no longer an asymmetric carbon atom, and as a result of the intermediate undergoing hydrogenation, the resulting compound of formula [I] will become a racemic modification. Needless to say, however, the process of this invention is not limited in any way by this presumed reaction mechanism.

In the optically active amino compound of formula [I], $R_1$ is preferably an alkyl group containing not more than 10 carbon atoms such as a methyl, ethyl, n- or tert-butyl, pentyl, or hexyl group, a cyclopentyl group, a cyclohexyl group, or a phenyl group, and $R_2$ is preferably a hydrogen atom, an alkyl group containing not more than 10 carbon atoms such as a methyl, ethyl, n- or iso-propyl, n-, iso- or tert-butyl, pentyl or hexyl group, cyclopentyl group, a cyclohexyl group, or a phenyl group.

Specific examples of the optically active amino compounds are 2-amino-1-propanol, 2-amino-1-butanol, 2-amino-1-pentanol, 2-amino-1-hexanol, 2-amino-1-heptanol, 2-amino-1-octanol, 2-amino-2-phenylethanol, 2-amino-2-cyclopentylethanol, 2-amino-2-cyclohexylethanol, 2-amino-2-cycloheptylethanol, 2-amino-2-cyclooctylethanol, 3-amino-2-methyl-2-butanol, 3-amino-2-methyl-2-pentanol, and 3-amino-2-methyl-2-hexanol. The above optically active amino compound may have any optical purity.

Thus, according to the process of this invention, a useful optical antipode amino compound can be obtained by optical resolution from the racemized optically active amino compound.

Taking up 2-amino-1-butanol as an example, $l$-2-amino-1-butanol is racemized by the process of this invention to form $dl$-2-amino-1-butanol, which is then formed into a salt that makes up a diasteromer with, for example dextrorotary tartaric acid. By crystallization, d-2-amino-1-butanol can be recovered. The d-2-amino-1-butanol is used as a material for preparing Ethmbutol useful as an antituberculous agent.

The following Examples illustrate the process of this invention in greater detail.

EXAMPLE 1

Preparation of Catalyst

A reduced cobalt catalyst was prepared as follows: 106 g of sodium carbonate ($Na_2CO_3$) was dissolved in 2 liters of water, and with stirring, a solution of 292 g of cobalt nitrate [$Co(NO_3)_2 \cdot 6H_2O$] in 2 liters of water was added dropwise over the course of about 2 hours. After the addition, the mixture was allowed to stand overnight. It was washed several times by decantation, filtered, and dried overnight at 110° C. The dried powder was pyrolyzed at 300° C., formed into a size of 5 mm in diameter of 2 mm in thickness, and reduced in a stream of hydrogen maintained at about 350° C.

Racemization

A 100 ml. vertically stirred-type autoclave was charged with 8.96 g of 2-amino-1-butanol having a specific rotation $[\alpha]_D^{20}$ of $-9.60°$, 26 g of ammonia and 3 g of the reduced cobalt catalyst prepared above. Then, hydrogen was introduced into the autoclave to a pressure of 50 atmospheres. The temperature was then raised to 200° C., and they were reacted at this temperature for 5 hours.

After the reaction, the ammonia was driven off, and the residual amount of 2-amino-1-butanol was determined by gas-chromatography. The reaction product was distilled to afford 6.1 g of racemized 2-amino-1-butanol having a boiling point of 50° to 83° C/10 mmHg.

The amount determined of 2-amino-1-butanol by gas chromatography was 5.08 g, and its specific rotation was $[\alpha]_D^{20} = -0.127°$ (not diluted).

The ratio of recovery of 2-amino-1-butanol was 56.6%, and the change rate of $[\alpha]_D^{20}$ was 98.6%.

$$\text{Recovvery ratio of 2-amino-1-butanol} = \frac{\text{Amount determined of 2-amino-1-butanol after the reaction}}{\text{Amount fed of 2-amino-1-butanol}} \times 100$$

Change rate of $[\alpha]_D^{20} =$ $$\left(1 - \frac{[\alpha]_D^{20} \text{ of 2-amino-1-butanol recovered by distillation}}{[\alpha]_D^{20} \text{ of 2-amino-1-butanol fed}}\right) \times 100$$

EXAMPLES 2 to 6

A catalyst was prepared as follows:

With stirring a solution of 288 g (0.99 mole) of cobalt nitrate [$Co(NO_3)_2 \cdot 6H_2O$] and 4 g (0.01 mole) of ferric nitrate [$Fe(NO_3)_3 \cdot 9H_2O$] in 2 liters of water was added dropwise to a solution of 109 g (1.03 moles) of sodium carbonate ($Na_2CO_3$) in 2 liters of water. The resulting precipitate was treated in the same way as in the preparation of the reduced cobalt catalyst in Example 1 to form a catalyst composed of Co—$Fe_2O_3$ (Co/Fe atomic ratio = 99/1). By the same precipitating method, Co—$Fe_2O_3$ catalysts of varying compositions were prepared. Using 3 g each of these catalysts, the same reaction as in Example 1 was performed under the conditions shown in Table 1. The results are shown in Table 1.

Table 1

| Example No. | 2AB* g | 2AB* $[\alpha]_D^{20}$ | Catalyst (Co:Fe atomic ratio) | $NH_3$ | Temperature (°C) | Hydrogen pressure (atms.) | Time (hr) | Amount determined of 2AB* (g) | $[\alpha]_D^{20}$ of recovered 2AB* | Recovery ratio of 2AB* (%) | Change ratio of $[\alpha]_D^{20}$ |
|---|---|---|---|---|---|---|---|---|---|---|---|
| 2 | 9.16 | −5.19° | Co-Fe$_2$O$_3$ (99:1) | 26 g | 200 | 50 | 5.0 | 6.84 | −1.03° | 74.7 | 80.0 |
| 3 | 9.09 | −5.19° | Co-Fe$_2$O$_3$ (99:1) | 28% aq.sol. 40 ml | 210 | 50 | 5.0 | 6.80 | −1.81° | 74.8 | 65.1 |
| 4 | 9.01 | −5.19° | Co-Fe$_2$O$_3$ (90:10) | 26 g | 200 | 50 | 5.0 | 6.00 | −0.445° | 66.6 | 91.3 |
| 5 | 9.11 | −5.19° | Co-Fe$_2$O$_3$ (90:10) | 26 g | 200 | 80 | 5.0 | 6.84 | −0.05° | 75.1 | 99.0 |
| 6 | 9.19 | −9.60 | Co-Fe$_2$O$_3$ (80:20) | 26 g | 200 | 50 | 5.0 | 8.54 | −0.275° | 92.9 | 97.1 |

*2AB = 2-amino-1-butanol

EXAMPLES 7 to 10

Optically active 2-amino-1-butanol was racemized at the temperature indicated in Table 2 using each of the Co—U, Co—Th and Ni—Fe catalysts of the compositions shown in Table 2 which were prepared in the same way as in Examples 2 to 6 except that uranyl nitrate or thorium nitrate was used instead of the ferric nitrate, or nickel nitrate was used instead of the cobalt nitrate. The results are shown in Table 2.

1. A process for racemizing optically active amino compounds, which comprises contacting an optically active compound of the formula

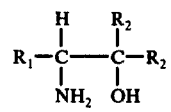

wherein $R_1$ is an alkyl containing not more than 10

Table 2

| Example No. | 2AB* g | 2AB* $[\alpha]_D^{20}$ | Catalyst | $NH_3$ | Temperature (°C) | Hydrogen pressure (atms.) | Time (hr) | Amount determined of 2AB* (g) | $[\alpha]_D^{20}$ of recovered 2AB* | REcovery ratio of 2AB* (%) | Change rate of $[\alpha]_D^{20}$ % |
|---|---|---|---|---|---|---|---|---|---|---|---|
| 7 | 9.06 | −5.19° | Co-U (90:10) | 26 g | 180 | 50 | 4 | 8.32 | −4.5° | 91.8 | 13.3 |
| 8 | 9.00 | −5.19° | Co-U (90-10) | 26 g | 200 | 50 | 4 | 3.62 | 0° | 40.2 | 100 |
| 9 | 8.97 | −5.19' | Co-Th (95-5) | 26 g | 200 | 50 | 5 | 1.79 | −0.064° | 20.0 | 98.8 |
| 10 | 8.07 | −5.19° | Ni-Fe (8:2) | 26 g | 220 | 50 | 5 | 2.85 | −0.381° | 35.3 | 92.7 |

*2AB = 2-amino-1-butanol

EXAMPLES 11 to 16

Each of 2-amino-1-butanols of varying specific rotation shown in Table 3 was racemized in the presence of ammonia and hydrogen using each of the various commercially available hydrogenation catalysts shown in Table 3. The reaction conditions and the results obtained are shown in Table 3.

carbon atoms and $R_2$ is hydrogen or an alkyl containing not more than 10 carbon atoms, with ammonia and hydrogen in the presence of a Co or Co-iron oxide catalyst which has activity in hydrogenation.

2. The process of claim 1 wherein said optically active amino compound is expressed by the following formula Table 3

| Example No. | 2AB* g | 2AB* $[\alpha]_D^{20}$ | Catalyst | $NH_3$ | Temperature (°C) | Hydrogen pressure (atms.) | Time (hr) | Amount determined of 2AB* (g) | $[\alpha]_D^{20}$ of recovered 2AB* | Recovery ratio of 2AB* (%) | Change ratio of $[\alpha]_D^{20}$ |
|---|---|---|---|---|---|---|---|---|---|---|---|
| 11 | 8.90 | +9.60 | Ph-C (5%) 1 g | 26 g | 150 | 50 | 5 | 8.69 | +8.99° | 97.6 | 63% |
| 12 | 8.90 | −6.26° | Ru-C (5%) 1 g | 26 g | 200 | 50 | 5 | 8.06 | −5.97 | 90.6 | 46% |
| 13 | 5.0 | +4.76° | RA-C (5%) 0.5 g | 28% aq.sol. 30 g | 250 | 10 | 6 | 1.7 | 0° | 34.0 | 100% |
| 14 | 5.0 | +4.76 | Raney nickel 1 g | 28% aq.sol. 20 g | 200 | 10 | 6 | 2.3 | +0.244° | 46.0 | 94.9% |
| 15 | 5.0 | +4.76 | Raney cobalt 1 g | 28% aq.sol. 20 g | 200 | 10 | 6 | 1.8 | +0.859 | 36.0 | 82.0% |
| 16 | 5.0 | +4.76 | Copper-chromite 1 g | 30 g | 200 | 30 | 6 | 3.0 | +4.15 | 60.0 | 12.8% |

What we claim is:

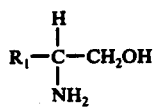

wherein $R_1$ is an alkyl group.

3. The process of claim 1 wherein said reaction is carried out at a temperature of 100° to 300° C.

4. The process of claim 1 wherein the ammonia is employed in an amount of at least 3 moles per mole of optically active amino compound.

5. The process according to claim 1 wherein the partial pressure of hydrogen is 10 to 150 atmospheres.

6. The process according to claim 4 wherein the partial pressure of hydrogen is 10 to 150 atmospheres.

7. The process of claim 1 wherein the catalyst is a cobalt catalyst which has activity in hydrogenation.

8. The process according to claim 1 wherein the catalyst is a cobalt-iron oxide catalyst which has activity in hydrogenation.

* * * * *